(12) United States Patent
Marton

(10) Patent No.: US 9,125,842 B2
(45) Date of Patent: Sep. 8, 2015

(54) AGENT AND METHOD FOR COLORING KERATIN FIBERS

(71) Applicant: GW COSMETICS GMBH, Leopoldsdorf (AT)

(72) Inventor: Istvan Marton, Vienna (AT)

(73) Assignee: GW COSMETICS GMBH, Leopoldsdorf (AT)

( * ) Notice: Subject to any disclaimer, the term of this patent is extended or adjusted under 35 U.S.C. 154(b) by 0 days.

(21) Appl. No.: 14/361,260

(22) PCT Filed: Nov. 26, 2012

(86) PCT No.: PCT/AT2012/050184
§ 371 (c)(1),
(2) Date: May 28, 2014

(87) PCT Pub. No.: WO2013/078492
PCT Pub. Date: Jun. 6, 2013

(65) Prior Publication Data
US 2014/0310888 A1  Oct. 23, 2014

(30) Foreign Application Priority Data
Nov. 28, 2011 (AT) .................................. 1752/2011

(51) Int. Cl.
*A61Q 5/10* (2006.01)
*A61K 8/97* (2006.01)
*A61K 8/368* (2006.01)
*A61K 8/49* (2006.01)
*A61K 8/19* (2006.01)

(52) U.S. Cl.
CPC ... *A61K 8/97* (2013.01); *A61K 8/19* (2013.01); *A61K 8/368* (2013.01); *A61K 8/498* (2013.01); *A61Q 5/10* (2013.01)

(58) Field of Classification Search
CPC ........... A61Q 5/10; A61K 8/97; A61K 8/922; A61K 2800/43
USPC ............... 8/405, 406, 410, 624, 646
See application file for complete search history.

(56) References Cited

U.S. PATENT DOCUMENTS

| | | | |
|---|---|---|---|
| 35,840 A | 7/1862 | Saur | 8/424 |
| 40,918 A | 12/1863 | Saur | 8/424 |
| 3,194,734 A | 7/1965 | Seemuller et al. | 8/423 |
| 6,099,591 A | 8/2000 | Matravers et al. | 8/408 |
| 2002/0152558 A1* | 10/2002 | Vidal et al. | 8/405 |
| 2003/0150067 A1* | 8/2003 | Morita et al. | 8/405 |
| 2006/0249170 A1* | 11/2006 | Kripp et al. | 132/202 |
| 2013/0255009 A1* | 10/2013 | Hu et al. | 8/425 |

FOREIGN PATENT DOCUMENTS

| | | |
|---|---|---|
| AU | B-61430/80 | 7/1984 |
| DE | 2806603 | 8/1979 |
| DE | 29805893 | 6/1998 |
| DE | 20314464 | 3/2004 |
| DE | 202004016367 | 4/2006 |
| EP | 0327345 | 8/1989 |
| EP | 2196180 | 6/2010 |
| FR | 2951940 | 10/2009 |
| WO | WO 2010/062138 A2 * | 6/2010 ............ A61Q 5/10 |

OTHER PUBLICATIONS

Ullmann's Encyclopedia of Industrial Chemistry, 3rd edition, vol. 10, p. 734 (English machine translation provided).
Redgrove, H.S. et al.:" Blonde or Brunette?: Hair-Dyes and Hair-Dyeing Chemistry and Technique", William Heinemann (Medical Books) Ltd., (1934), 15 pages.
Karamac, M. et al.: "Content of Gallic Acid in Selected Plant Extracts", Polish Journal of Food and Nutrition Sciences, vol. 15/56, No. 1, (2006), pp. 55-58.
SCCS (Scientific Committee on Consumer Safety), "Opinion on oxidative hair dye substances and hydrogen peroxide used in products to colour eyelashes", (Oct. 12, 2012), pp. 1-21.

* cited by examiner

*Primary Examiner* — Eisa Elhilo
(74) *Attorney, Agent, or Firm* — Norton Rose Fulbright US LLP

(57) ABSTRACT

The object of the invention is a ready to use coloring composition containing at least 0.02 wt % of at least one compound chosen from the group consisting of catechins, gallic acid, gallates, and mixtures thereof, together with a silver salt, and a product for simultaneous or timewise separate use comprising two components A and B.

21 Claims, No Drawings

AGENT AND METHOD FOR COLORING KERATIN FIBERS

This application is a national phase application under 35 U.S.C. §317 of International Application No. PCT/AT2012/050184 filed 26 Nov. 2012, which claims priority to Austrian Patent Application No. A 1752/2011 filed 28 Nov. 2011. The entire contents of each of the above-referenced disclosures is specifically incorporated herein by reference without disclaimer.

This invention concerns a composition for permanent coloring of keratin fibers, especially for permanent coloring of eyelashes and eyebrows.

According to Wilfried Umbach, Cosmetics—Development, Manufacturing, and Use of Cosmetic Agents, 2nd edition, Georg Thieme Publishers, Stuttgart, 1995 [in German], hair color can be divided into temporary, semi-permanent, and permanent colors, according to the coloring and the durability, each with regard to the number of possible shampoos. A temporary hair color disappears after the first washing with a shampoo and is based on physical adherence of a colorant. A semi-permanent hair color lasts roughly two to ten shampoos and a permanent color withstands more than ten shampoos. In the case of a permanent coloring, colorants are chemically bonded to certain amino acids in the hair or, in the case of bleaching, pigments in the hair are oxidized.

Oxidation dyes, which are mixed with hydrogen peroxide immediately before use, have been used up to now for permanent coloring of eyebrows and eyelashes. The color in this case arises through oxidation of a mixture of certain developer and coupler substances in the presence of the hydrogen peroxide.

An agent for oxidative coloring of hair, which is mixed with a colorant immediately before use by mixing a developer lotion and a colorant and is adjusted to an acid pH value, is known from DE 298 05 893. Through such an oxidative coloring of hair, a hair colorant can indeed be made that has a pH value between 5 and 7, but the preparation process is relatively complicated and also the application time is comparatively long, so that the hair dye is not very suitable for coloring eyelashes or eyebrows. Such an oxidative coloring with hydrogen peroxide and colorants can currently only be employed professionally and possibly will be banned altogether.

Furthermore, a cosmetic preparation containing at least one colorant that is insoluble in the preparation and that gives fluorescence effects under UV light is known from DE 203 14 464; with this preparation, portions of the skin or hair can be decoratively colored. However, such agents have only limited durability and therefore must be frequently refreshed, which is perceived as extravagant.

Further, an agent for coloring hair that comprises a colorant, ammonia, an alcohol, tannic acid, and a shampoo, is specified in AU-B-61430/80. The agent for coloring the hair is applied to the hair in order to obtain the desired color.

U.S. Pat. No. 3,194,734 discloses hair coloring compositions that contain ammonia and dihydroxy-5,6-indoles together with an oxidizing agent like hydrogen peroxide.

In accordance with DE 20 2004 016 367 U1, an agent for coloring hair comprises an aqueous solution containing tannin (tannic acid) and ammonia. With this agent the hair becomes softened and then can be colored in a two-step process, for example, with silver nitrate gel or other colorants.

The use of inorganic silver nitrate solutions or other metal salts mixed with a pyrogallol solution as colorant has long been known, for example, from Ullmann's Encyclopedia of Industrial Chemistry, 3rd edition, Volume 10, p. 734 [in German]. In this case the silver ions react with the amino acid cysteine in the hair, through which colors between blond and black can be set.

On the other hand, for nuanced coloring of keratin fibers, thus for semi-permanent coloring, colorants that have a high affinity to the keratin of the hair are used, where these colorants bond by a physical bond. Nitrophenylenediamines, azoimine and quinoneimine dyes in combination with organic solubilizers like glycol ether or polypropylene are used as synthetic semi-permanent hair colorings; the natural semi-permanent hair colorings henna (leaves and stems of *Lawsonia alba* Lam. or *L. inermis* L.), reng (from the indigo plant), chamomile (Apigenin), wood and bark extracts, and rastik (pyrogallol and iron or copper salts) have lost their importance today.

The problem of the invention is to create a hydrogen peroxide-free composition for permanent coloring of keratin fibers, especially for permanent coloring of eyelashes and eyebrows, which ensures consistent color quality and permanency of the color of the eyebrows and eyelashes.

This problem is solved in accordance with the invention in that the ready to use coloring composition contains at least 0.02 wt % of at least one compound chosen from the group consisting of catechins, gallic acid, gallates, and mixtures thereof, together with a silver salt. The organic ingredients (catechins, gallic acid, gallates, and mixtures thereof) can preferably originate from extracts of plants such as witch hazel (Hamamelis), white tea, green tea, and oolong, vegetables, wine, the wood of the cutch tree *Acacia catechu*, and fruit varieties like apples, apricots, pears, blackberries, strawberries, raspberries, black currents, peaches, plums, quince, sour cherries, gooseberries, sweet cherries, pomegranates, and grapes. The use of extracts of witch hazel, green tea, acacia, and pomegranate, and mixtures thereof is especially preferred. The catechins can also be synthetic in origin. Gallates are derivatives of gallic acid and are present, for example, in oak bark and oak apples as well as green tea and oolong. Synthetic gallates can also be preferably used, with methyl gallate, ethyl gallate, propyl gallate (E 310), octyl gallate (E 311) and dodecyl gallate (E 312), and mixtures thereof being preferred. Propyl gallate is especially preferred. The ready to use coloring composition can be prepared before use by mixing individual components comprising at least one compound selected from the group consisting of catechins, gallic acid, gallates, and mixtures thereof (component A) on the one hand and a silver salt (component B) on the other hand, or the individual components can be applied to the eyebrows and eyelashes in any order. The individual components can be in liquid, cream, or gel form. For selling, the ingredients of component A can also be in powder form, the powder being made ready to use before application or mixing by dissolving or dispersing it in one or more suitable solvents or vehicles, for example, water.

Preferably in accordance with the invention, the ready to use coloring composition contains silver nitrate as the silver salt, and especially preferably the silver nitrate is in gel form at least in the form of component B.

According to another preferred embodiment of this invention, the ready to use coloring composition contains, besides the at least 0.02 wt % of at least one compound chosen from the group consisting of catechins, gallic acid, gallates, and mixtures thereof, additionally at least one compound chosen from the group comprising p-phenylenediamine, p-toluenediamine, N-phenyl-p-phenylenediamine, hydroxyethyl-p-phenylenediamine, N,N'-bishydroxyethyl-p-phenylenediamine, 2-chloro-p-phenylenediamine, triaminopyrimidine, tetraaminopyrimidine, m-aminophenol, p-aminophenol, o-aminophenol, resorcinol, 2-methylresorcinol, 4-chlororesorcinol, 2,6-diaminopyridine, 2,6-dimethoxy-3,5-diaminopyridine, 2-amino-3-hydroxypyridine, 2-methyl-5-hydroxyethylaminophenol, N,N'-bishydroxyethyl-p-phenylenediamine, 2,4-diaminophenoxyethanol, 2-amino-4-hydroxyethylaminoanisol sulfate, 4-amino-m-cresol, 6-amino-m-cresol, phenylmethylpyrazolone, 4-amino-2-hydroxytoluene, p-methylaminophenol, hydroxybenzomorpholine, 1,3-bis(2,4-diaminophenoxy)propane, 6-methoxy-2-methylamino-3-aminopyridine, 5-amino-4-chloro-o-cresol, 3-amino-2,4-dichlorophenol, 1-naphthol, 1,5-naphthalenediol, 2,7-naphthalenediol, 1-hydroxyethyl-4,5-diaminopyrazole sulfate, 2,2'-methylenebis-4-aminophenol, 2-methyl-1-naphthol, 1-acetoxy-2-methoxynaphthalene, and mixtures thereof.

The pH of the ready to use coloring composition lies in the range of about 5 to 9, preferably between about 6 and 8. The ready to use coloring composition can contain additional ingredients such as pigments, surfactants, thickeners, emulsion bases, solvents, preservatives, as well as sodium sulfite.

According to a preferred embodiment of this invention, the ready to use coloring composition comprises as component A between 0.1 wt % and 30 wt % of at least one compound chosen from the group consisting of catechins, preferably in an amount of 1 to 30 wt %, especially preferably 2 to 10 wt %, gallic acid, preferably in an amount of 0.1 to 5 wt %, especially preferably 0.3 to 3 wt %, gallates, preferably in an amount of 0.1 to 5 wt %, especially preferably 0.3 to 3 wt %, and mixtures thereof, preferably between 2 and 5 wt %, where the data in wt % refer to component A.

Provided in accordance with the invention is also a product for simultaneous or timewise separate use comprising two components A and B, where component A comprises at least 0.02 wt %, preferably between 0.1 and 30 wt %, especially preferably in a total amount between 2 and 5 wt % of at least one compound chosen from the group consisting of catechins, preferably in an amount of 1 to 30 wt %, especially preferably 2 to 10 wt %, gallic acid, preferably in an amount of 0.1 to 5 wt %, especially preferably 0.3 to 3 wt %, gallates, preferably in an amount of 0.1 to 5 wt %, especially preferably 0.3 to 3 wt %, and/or mixtures thereof, where the data in wt % refer to component A, and component B comprises a preparation containing silver nitrate in a basic solution with a pH between 7 and 10, preferably 8 to 9. The two components can each be in the form of an aqueous solution, an emulsion, or a gel, or the ingredients of component A can also be in powder form, the powder being made ready to use before application or mixing by dissolving or dispersing it in one or more suitable solvents or vehicles, for example water, and components A and B can also contain for stabilization thickeners or other ingredients.

According to a preferred embodiment, component B is in the form of an ammoniacal solution.

Preferably the component B contains silver nitrate in an amount of 2 to 3 wt %, preferably 1.8 to 2.2 wt %, where the data in wt % refer to component B.

The ready to use coloring composition after application, as mentioned either after mixing the components and then applying them or after applying the individual components separately in any order, can advantageously be left to act for a total time of 3 to 30 min, preferably between 10 and 20 min.

This invention will now be explained in more detail with reference to the following examples, to which, however, it is not intended to be limited.

In the examples the extracts or compounds from the following manufacturers were used:

| | |
|---|---|
| *Acacia catechu* extract | *Acacia catechu* BE 3% Catechins, Denk Ingredients GmbH, Munich (DE) |
| Green tea extract I | Green Tea Dry Extract 90, Biopole, Clermont-Limagne (FR) |
| Green tea extract II | Green Tea Extract 50% Polyphenols, Denk Ingredients GmbH, Munich (DE) |
| Witch hazel extract | *Hamamelis* Leaves Extract, Denk Ingredients GmbH, Munich (DE) |
| Pomegranate extract | Pomgranate Extract WS, Denk Ingredients GmbH, Munich (DE) |
| Gallic acid | Orion Chemicals Metalchem Spain, Barcelona (ES) |
| Propyl gallate | Syntharo Fine Chemicals, Troisdorf (DE) |
| Ethyl gallate | Sigma-Aldrich Produktion GmbH, Buchs (CH) |

EXAMPLE 1

| Color (Component A) | |
|---|---|
| Propyl gallate (E 310) | 0.3 wt % |
| *Acacia catechu* extract | 0.4 wt % |
| Witch hazel extract | 0.2 wt % |
| Ammonium acryloyldimethyl taurate/VP copolymer | 1.0 wt % |
| Demineralized water, to | 100.0% wt % |

EXAMPLE 2

| Color (Component A) | |
|---|---|
| Green tea extract | 3.0 wt % |
| Ethyl gallate | 0.8 wt % |
| Ammonium acryloyldimethyl taurate/VP copolymer | 1.0 wt % |
| Demineralized water, to | 100.0% wt % |

EXAMPLE 3

| Color (Component A) | |
|---|---|
| Witch hazel extract | 2.0 wt % |
| Ammonium acryloyldimethyl taurate/VP copolymer | 0.8 wt % |
| p-Phenylenediamin | 0.3 wt % |
| Gallic acid | 0.2 wt % |
| Demineralized water, to | 100.0% wt % |

EXAMPLE 4

| Color (Component A) | |
|---|---|
| Witch hazel extract | 0.5 wt % |
| Green tea extract II | 0.5 wt % |
| Pomegranate extract | 0.5 wt % |
| *Acacia catechu* extract | 0.5 wt % |
| Ammonium acryloyldimethyl taurate/VP copolymer | 1.0 wt % |
| Demineralized water, to | 100.0% wt % |

EXAMPLE 5

| Color (Component A) | |
| --- | --- |
| Witch hazel extract | 10.0 wt % |
| Ammonium acryloyldimethyl taurate/VP copolymer | 0.9 wt % |
| Demineralized water, to | 100.0% wt % |

EXAMPLE 6

| Silver nitrate gel (Component B) | |
| --- | --- |
| Silver nitrate | 3.0 wt % |
| Carbomer | 0.7 wt % |
| Ammonia, 25% | 3.5 wt % |
| Demineralized water, to | 100.0 wt % |

EXAMPLE 7

| Silver nitrate gel (Component B) | |
| --- | --- |
| Silver nitrate | 2.2 Gew. % |
| Carbomer | 0.7 Gew. % |
| Ammonia, 25% | 3.5 Gew. % |
| Demineralized water, to | 100.0 Gew. % |

EXAMPLE 8

| Silver nitrate gel (Component B) | |
| --- | --- |
| Silver nitrate | 1.8 Gew. % |
| Carbomer | 0.7 Gew. % |
| Ammonia, 25% | 3.5 Gew. % |
| Demineralized water, to | 100.0 Gew. % |

EXAMPLE 9

| Silver nitrate gel (Component B) | |
| --- | --- |
| Silver nitrate | 1.0 Gew. % |
| Carbomer | 0.7 Gew. % |
| Ammonia, 25% | 3.5 Gew. % |
| Demineralized water, to | 100.0 Gew. % |

After being applied separately (first application of component A in about 50% by weight, then blotting the lashes, then application of component B in about 50% by weight), components A and B were left to act for a total time of between 10 and 20 min. The result was in each case a clear permanent coloring of the eyelashes with a color that depended on the extract that was used (catechins, gallic acid, gallates, and mixtures thereof) and its concentration in component A and the concentration or applied amount of silver nitrate in component B.

The invention claimed is:

1. A composition comprising:
   at least one component A comprising at least 0.02 wt % of at least one catechin, gallic acid, gallate, or a mixture thereof, which originate from plant extracts; and
   at least one component B comprising a silver salt in the form of an ammoniacal solution, wherein the composition can dye keratin fibers.

2. The composition of claim 1, wherein the plant extract is further defined as an extract of witch hazel, oak bark, white tea, green tea, oolong tea, wine, wood of a cutch tree *Acacia catechu*, apple, oak apple, apricot, pear, blackberry, strawberry, raspberry, black current, peach, plum, quince, sour cherry, gooseberry, sweet cherry, pomegranate, or grape.

3. The composition of claim 2, wherein component A comprises at least one catechin, gallic acid, gallate, or a mixture thereof, which originate from an extract of witch hazel, green tea, acacia, and/or pomegranate.

4. The composition of claim 1, wherein component A further comprises at least one of p-phenylenediamine, p-toluenediamine, N-phenyl-p-phenylenediamine, hydroxyethyl-p-phenylenediamine, N,N'-bishydroxyethyl-p-phenylenediamine, 2-chloro-p-phenylenediamine, triaminopyrimidine, tetraaminopyrimidine, m-aminophenol, p-aminophenol, o-aminophenol, resorcinol, 2-methylresorcinol, 4-chlororesorcinol, 2,6-diaminopyridine, 2,6-dimethoxy-3,5-diaminopyridine, 2-amino-3-hydroxypyridine, 2-methyl-5-hydroxyethylaminophenol, N,N'-bishydroxyethyl-p-phenylenediamine, 2,4-diaminophenoxyethanol, 2-amino-4-hydroxyethylaminoanisol sulfate, 4-amino-m-cresol, 6-amino-m-cresol, phenylmethylpyrazolone, 4-amino-2-hydroxytoluene, p-methylaminophenol, hydroxybenzomorpholine, 1,3-bis(2,4-diaminophenoxy)propane, 6-methoxy-2-methylamino-3-aminopyridine, 5-amino-4-chloro-o-cresol, 3-amino-2,4-dichlorophenol, 1-naphthol, 1,5-naphthalenediol, 2,7-naphthalenediol, 1-hydroxyethyl-4,5-diaminopyrazole sulfate, 2,2'-methylenebis-4-aminophenol, 2-methyl-1-naphthol, and 1-acetoxy-2-methoxynaphthalene.

5. The composition of claim 1, further defined as having a pH in the range of about 5 to 9.

6. The composition of claim 5, further defined as having a pH in the range of about 6 to 8.

7. The composition of claim 1, further defined as comprising at least one pigment, surfactant, thickener, emulsion base, solvent, preservative, and/or sodium sulfite.

8. The composition of claim 1, further defined as comprising a gallate in component A.

9. The composition of claim 8, further defined as comprising the gallate in an amount of 0.1 to 5 wt % of component A.

10. The composition of claim 9, further defined as comprising the gallate in an amount of 0.3 to 3 wt % of component A.

11. A method comprising:
    obtaining a composition of claim 1; and
    using the composition to dye keratin fibers.

12. The method of claim 11, further comprising mixing component A and component B to create the composition.

13. A product comprising:
    a component A comprising a gallate originating from plant extracts in an amount of 0.02 wt % of component A; and
    a component B comprising silver nitrate in a basic ammoniacal solution having a pH in the range of about 7 to 10.

14. The product of claim 13, wherein component A is further defined as comprising the gallate in an amount of 0.1 to 5 wt % of component A.

15. The product of claim 14, wherein component A is further defined as comprising the gallate in an amount of 0.3 to 3 wt % of component A.

16. The product of claim 13, wherein component B is further defined as having a pH in the range of about 8 to 9.

17. The product of claim 13, wherein components A and B are in the form of an aqueous solution, an emulsion, or a gel, or component A is in powder form.

18. The product of claim 13, wherein at least one of component A and component B comprises a thickener.

19. The product of claim 13, wherein component B contains silver nitrate in an amount of 2 to 3 wt % of component B.

20. The product of claim 19, wherein component B contains silver nitrate in an amount of 1.8 to 2.2 wt % of component B.

21. The product of claim 19, wherein component A and component B are in separate containers.

\* \* \* \* \*